(12) United States Patent
Colabufo et al.

(10) Patent No.: US 10,663,458 B2
(45) Date of Patent: May 26, 2020

(54) METHOD AND KIT FOR DETERMINATION OF FREE COPPER IN SERUM

(71) Applicant: IGEA RESEARCH CORPORATION, Miami, FL (US)

(72) Inventors: Nicola Antonio Colabufo, Triggiano (IT); Rosanna Squitti, Rome (IT)

(73) Assignee: IGEA RESEARCH CORPORATION, Miami, FL (US)

( * ) Notice: Subject to any disclaimer, the term of this patent is extended or adjusted under 35 U.S.C. 154(b) by 153 days.

(21) Appl. No.: 14/441,071

(22) PCT Filed: Nov. 7, 2012

(86) PCT No.: PCT/EP2012/072063
§ 371 (c)(1),
(2) Date: May 6, 2015

(87) PCT Pub. No.: WO2014/071973
PCT Pub. Date: May 15, 2014

(65) Prior Publication Data
US 2015/0276722 A1    Oct. 1, 2015

(51) Int. Cl.
G01N 33/00    (2006.01)
G01N 33/52    (2006.01)
G01N 33/84    (2006.01)

(52) U.S. Cl.
CPC ............ *G01N 33/52* (2013.01); *G01N 33/84* (2013.01); *G01N 2800/2821* (2013.01)

(58) Field of Classification Search
CPC .................................................. G01N 33/52
USPC .......................................................... 436/74
See application file for complete search history.

(56) References Cited

U.S. PATENT DOCUMENTS

| | | | | |
|---|---|---|---|---|
| 4,843,017 A | * | 6/1989 | Oberhardt | B01D 61/18 210/321.6 |
| 5,711,915 A | * | 1/1998 | Siegmund | G01N 33/54373 422/68.1 |
| 2008/0026478 A1 | * | 1/2008 | Czerney | C07D 311/56 436/86 |

(Continued)

FOREIGN PATENT DOCUMENTS

KR    2011-0068259    5/2011

OTHER PUBLICATIONS

Hyo Sung Jung, Pil Seung Kwon, Jeong Won Lee, Jae Il Kim, Chang Seop Hong, Jong Wan Kim, Shihai Yan, Jin Yong Lee, Jung Hwa Lee, Taiha Joo, and Jong Seung Kim "Coumarin-Derived Cu2+-Selective Fluorescence Sensor: Synthesis, Mechanisms, and Applications in Living Cells" J. Am. Chem. Soc. 9 vol. 131, No. 5, 2009.*

(Continued)

*Primary Examiner* — Christopher Adam Hixson
*Assistant Examiner* — Emily R. Berkeley
(74) *Attorney, Agent, or Firm* — Sterne, Kessler, Goldstein & Fox P.L.L.C.

(57) ABSTRACT

The present invention relates to a new method for the determination of free copper in serum. In particular to a method with a high degree of sensitivity and accuracy for the determination of free copper in serum samples of patients with Alzheimer's disease and Wilson's disease and other forms of free copper dyshomeostasis. The invention also relates to kits for the determination of free copper in serum comprising filter devices and coumarin fluorescent probe.

15 Claims, 5 Drawing Sheets

(56) References Cited

U.S. PATENT DOCUMENTS

| | | | |
|---|---|---|---|
| 2008/0268491 A1 | 10/2008 | Kanzer et al. | |
| 2009/0298180 A1* | 12/2009 | Cattadoris | B01F 11/0065 435/383 |
| 2010/0129290 A1 | 5/2010 | Yezdimer et al. | |
| 2010/0227794 A1 | 9/2010 | Yezdimer et al. | |

OTHER PUBLICATIONS

Christos Davatzikos, Feng Xu, Yang An, Yong Fan and Susan M. Resnick "Longitudinal progression of Alzheimer's-like patterns of atrophy in normal older adults: the SPARE-AD index" Brain 2009: 132; 2026-2035.*

Vishal Desai and Stephen G Kaler "Role of copper in human neurological disorders." Am J Clin Nutr 2008; 88(suppl):855S-8S.*

Zhaojuan Zhou, Na Li, Aijun Tong "A new coumarin-based fluorescence turn-on chemodosimeter for Cu2+ in water" Analytica Chimica Acta 702 (2011) 81-86.*

Thorslund et al. Biomed Microdevices (2006) 8: 73-79 (Year: 2006).*

Int'l Search Report for PCT/EP2012/072063, four pages, dated Jun. 7, 2013.

Jung et al. "Coumarin-derived $Cu^{2+}$-selective fluorescence sensor: Synthesis, mechanisms, and applications in living cells" *Journal of the American Chemical Society*, vol. 131, No. 5, pp. 2008-2012 (Feb. 2009).

Selimovic et al. "Research highlights" *Lab on a Chip*, vol. 12, No. 3, p. 503 (Jan. 2012).

Thorslund et al. "A hybrid poly(dimethylsiloxane) microsystem for on-chip whole blood filtration optimized for steroid screening" *Biomedical Microdevices*, vol. 8, No. 1, pp. 73-79 (Mar. 2006).

Zhou et al. "A new coumarin-based fluorescence turn-on chemodosimeter for Cu in water" *Analytica Chimica Acta*, vol. 702, No. 1, pp. 81-86 (Jun. 2011).

* cited by examiner

METHOD AND KIT FOR DETERMINATION OF FREE COPPER IN SERUM

This application is the U.S. national phase of International Application No. PCT/EP2012/072063, filed 7 Nov. 2012; the entire contents of which is hereby incorporated by reference.

TECHNICAL FIELD

The present invention relates to a new method for the determination of 'free' copper, the portion of serum copper not structurally bound to ceruloplasmin, recently named also 'labile' copper in serum. In particular to a method with a high degree of sensitivity and accuracy for the determination of free copper in serum samples of patients with Alzheimer's disease. The invention also relates to kits for the determination of free copper in serum comprising filter devices and coumarin fluorescent probe.

BACKGROUND OF THE INVENTION

The determination of serum copper is of primary importance in a large number of diseases as for example in the Alzheimer's disease (AD). Alzheimer's disease is a neurological disorder characterized by memory loss and progressive dementia. The late onset form of the disease is sporadic and has a complex disease aetiology, with familiarity and age as the most widely accepted risk factors. The cause of the disease appears closely related to the aggregation within the brain of the beta-amyloid (Aβ) peptide and tau proteins in neurofibrillary tangles. Moreover, the epsilon 4 allele of the apolipoprotein E (APOE) gene has been proven to increase Alzheimer's Disease risk and decrease the age of onset, even though it accounts only for a percentage of Alzheimer's Disease heritability, leaving several genetic risk factors to be identified. The 'amyloid cascade', which has been claimed as the most popular Alzheimer hypothesis, has now taken many forms as new details about the disease emerge. In fact, diverse pathogenetic pathways have been postulated to contribute to Alzheimer's Disease onset and progression. For example, besides Aβ oligomers and toxic tau aggregates, oxidative damage, aberrant inflammation or impaired energy metabolism have been pointed out among the pathogenic pathways involved in the disease cascade that need to be targeted. There is abundant evidence that oxidative stress, mainly via metal redox reactions, can cause damage to the Alzheimer's Disease brain. Specifically, it has been proposed that the hyper metallization of the Aβ peptide can be at the basis of redox cycles of oxidative stress and $H_2O_2$ production, Aβ oligomer formation and precipitation. A derangement of metal homeostasis leading to a labile pool of copper may feed the brain copper reservoir which can enter Aβ-oxidative stress cycles, generating pleiotropic effects on the Alzheimer's Disease cascade. This notion is now sustained by diverse lines of evidence showing that copper is slightly but significantly increased in Alzheimer's Disease, that a specific and relative high increase in the serum pool of copper non-bound to ceruloplasmin (also named 'free' copper), is associated with some typical signs and cerebrospinal fluid markers of Alzheimer's Disease and it is already evident in subjects complaining very mild cognitive impairments. Even though copper dysfunction cannot be assumed as the only determinant of the disease, its causative, rather than associated, role as an important risk factor for Alzheimer's Disease can be claimed, since it appears sustained by solid clinical, epidemiological, experimental, meta-analysis and genetic evidence.

Ceruloplasmin is the major copper-carrying protein in the blood, it is the main ferroxidase protein in serum, and it binds structurally 6 atoms of copper, to form an active holo-form of the protein, which can account for 85-95% of circulating copper, the remaining being free copper. In fact in previous studies the inventors used to estimate free copper starting from copper and ceruloplasmin measures, with the calculation as follows: serum copper concentration were double check by measured them either with the atomic absorption spectroscopy technique utilizing a Perkin Elmer AANALYST 300 atomic absorption spectrophotometer equipped with a graphite furnace with platform HGA 800 graphite tube, or according to the colorimetric method of Abe et al. Clin Chem 1989 (Randox Laboratories, Crumlin, UK); ceruloplasmin was analyzed by immunoturbidimetry assay (Horiba ABX, Montpellier, France) according to Wolf PI Crit Rev Clin Lab Sci 1982, for each serum copper and ceruloplasmin pair it has been computed the amount of copper bound to ceruloplasmin (CB) and the amount of copper not bound to ceruloplasmin ('free' copper) following standard procedures disclosed in Walsh et al. Ann Clin Biochem 2003. This calculation expresses 'free' copper in μmol/L and is based on the evidence that ceruloplasmin contains 0.3% copper.

Moreover, the inventors have recently set up an automated procedure to measure ceruloplasmin oxidase activity which utilizes o-diansidine dihydrochloride as a substrate, according to previous methods. In fact, it is well known that values of ceruloplasmin obtained immunologically, as we showed them in our previous studies, result in higher values than those obtained enzymatically, i.e., monitoring the protein's oxidase activity. This is because the apo-form of ceruloplasmin is biologically inactive. As a consequence the values of free copper derived by the method and calculation reported above are underestimated.

However, quantification of ceruloplasmin by the enzymatic method based on standard ceruloplasmin solutions has not been considered in the state of the art, because of its cost, the variable purity of commercially available ceruloplasmin and the general recommendation to report serum enzymes in International Units (UI). Previously the inventors have tried to quantify the amount of ceruloplasmin starting from the protein's oxidase activity with a commercial standard (Human Serum Ceruloplasmin, Sigma-Aldrich), but the spectroscopic inspection of the latter revealed a decay in the protein peak of absorbance in day-to-day assays, decreasing the confidence in using the enzymatic detection to quantify the protein amount, necessary to estimate the free copper value.

Hyo Sung Jung et al. (*J. Am. Chem. Soc.* 2009) disclosed the synthesis and the use of different coumarin probes for the determination of free copper in biological systems.

Scope of the present invention is to provide novel methods and kits to measure directly free copper in serum avoiding the underestimation or overestimation of free copper that occur in the methods of prior art.

SUMMARY OF THE INVENTION

The invention relates to an in vitro method and a kit for the determination of free copper in serum. As also showed in the examples, the inventors found that using several methods to separate the serum from the whole blood a loss of free copper between 10% and 20% occurs. Moreover the inventors found that using different fluorescent probes apt to bind copper, nonspecific interaction between the probes and serum occurs.

The invention described herein is based on the selection of several parameters to separate the serum from the whole blood using a filter membrane and the selection of a specific class of switch-off fluorescent probe for detecting free copper. The use of a coumarin fluorescent probe under the conditions set by the present application, allows the determination of free copper in blood samples with a high degree of accuracy and sensitivity avoiding the loss of free copper during separation of the serum from the whole blood.

Hence, object of the present invention is an in vitro method for determining the concentration of free copper in a blood sample comprising the following steps:

a) separating the serum from the whole blood of said sample with a membrane filter having a pore size between 0.1-0.5 µm using a filtering speed between 200 and 500 microliters per minute;

b) determining the concentration of free copper in the serum sample obtained in step a) using a coumarin fluorescent probe.

A further object of the invention is an in vitro method for determining the concentration of free copper for the confirmation of a clinical diagnosis of Alzheimer's Disease in a patient suspected of having Alzheimer's Disease comprising the same steps a) and b) and a further step c) of comparing the value determined in step b) with a threshold value (cut-off), wherein a higher concentration of free copper confirms the clinical diagnosis of Alzheimer's Disease.

A further object of the invention is an in vitro method for determining the concentration of free copper for the prognosis of Alzheimer's Disease in a patient wherein the steps a) and b) of the method are repeated on blood samples of said patient collected in subsequent moments and evaluating the progression in time of the concentration of free copper in the serum samples of said patient.

A further object of the invention is an in vitro method for determining the concentration of free copper for the prediction of the conversion form Mild Cognitive Impairment (MCI) to Alzheimer's disease in a patient suffering of Mild Cognitive Impairment comprising the same steps a) and b) and a further step c) of comparing the value determined in step b) with a threshold value (cut-off), wherein a higher concentration of free copper indicates the conversion from Mild Cognitive Impairment to Alzheimer's disease.

A further object of the invention is a kit for the detection of free copper in serum comprising one or more filter devices with a membrane filter having a pore size between 0.1-0.5 µm and one or more coumarin fluorescent probes.

DETAILED DESCRIPTION OF THE INVENTION

As previously indicated, the present invention relates to an in vitro method for the determination of the concentration of the free copper in a blood sample. In the present description the term "free copper" means copper in general circulation which is not structurally bound to ceruloplasmin. It is also recently named 'labile' copper, referring to its properties to be labile bound to albumin, small peptides, amino acids and other micro-nutrients and to be easy exchangeable among them. Free copper is a small molecular weight copper which can easily reach tissues among which the brain, crossing the blood brain barrier It is also one the seven marker utilized for posing the clinical diagnosis of Wilson's disease, the paradigmatic disease for copper toxicosis or accumulation.

In order to separate the serum from the whole blood, the method comprises a first step of (a) separating the serum from the whole blood filtering the blood sample using a membrane filter having a pore size between 0.1-0.5 μm, preferably between 0.1-0.2 μm, more preferably between 0.1-0.15 μm. The membrane filter is for example a polycarbonate membrane filter.

The filtering speed is between 200 and 500 μl per minute, for example 250, 300, 350, 400, 450 μl/min.

Figure 4:
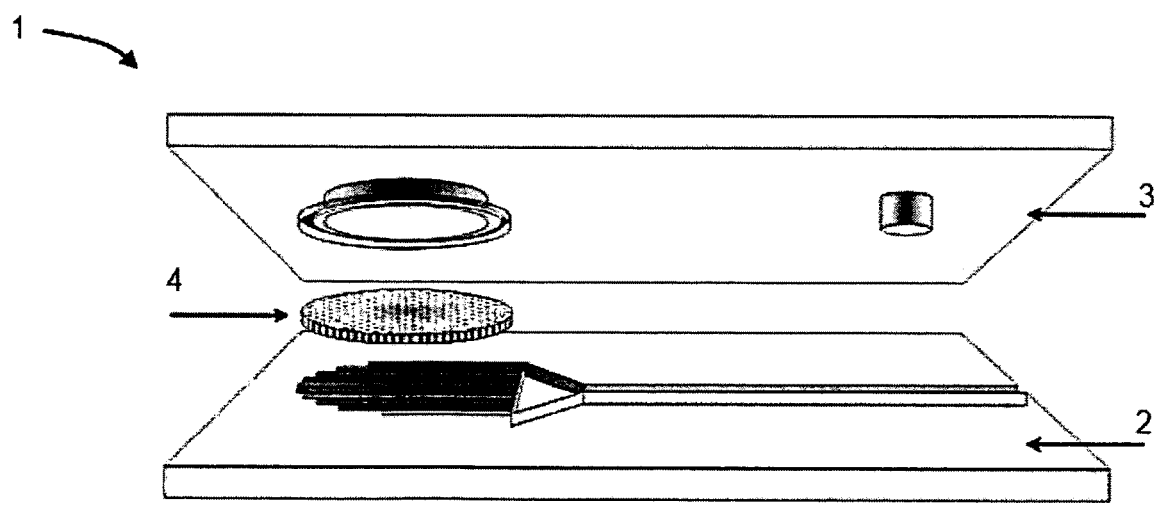
FIG. 4 shows a filter device for use in one embodiment of the present invention.

According to one embodiment of the present invention the membrane filter is in a filter device (FIG. 4). An example of a filter device 1 suitable to use in the method of the present invention comprises a bottom 2, including one or more microchannels, and a lid 3; wherein said membrane filter 4 is incorporated into said lid and over said microchannels. The membrane filter is incorporated into the lid before the two layers are bonded together.

According to one embodiment of the present invention the filter device is a poly (dimethylsiloxane) (PDMS) casted device.

According to another embodiment of the present invention the filter device is a microfluidic device disclosed in Thorslund S. et al, Biomed Microdevices (2006) herein incorporated by reference.

Before performing the separation step a) the blood sample may be subjected to one or more optional steps as known in the art to obtain a sample more suitable to separate the serum from the whole blood.

The method comprises a second step of (b) determining the free copper in the serum sample obtained in step (a) using a coumarin fluorescent probe. Coumarin fluorescent probe are chelating fluorescent probes for which a decay in fluorescence emission could be recorded when it binds [$Cu^{++}$]. The Coumarin fluorescent probe may be selected for example from compounds having the following general structural formula:

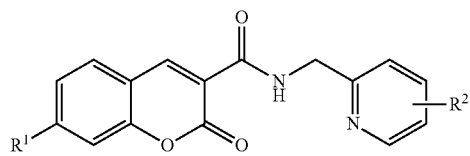

wherein
$R^1$ is $N[(CH_2)nCH_3]_2$ with n from 0 to 5;
$R^2$ is H, F, Cl, Br, NO2, OCH3, cyclohexyl;

According to one embodiment of the present invention said coumarin fluorescent probe is selected from the group above wherein $R^1$ is $N[(CH_2)nCH_3]_2$ with n=1 and $R^2$ is H, F, Cl, Br, NO2, OCH3, cyclohexyl either in ortho-, para- or meta-. position.

According to another embodiment of the present invention said coumarin fluorescent probe is selected from the group above wherein $R^1$ is $N[(CH_2)nCH_3]_2$ with n=2 and $R^2$ is H, F, Cl, Br, NO2, OCH3, cyclohexyl either in ortho-, para- or meta-. position.

According to another embodiment of the present invention said coumarin fluorescent probe is selected from the group above wherein $R^1$ is $N[(CH_2)nCH_3]_2$ with n=3 and $R^2$ is H, F, Cl, Br, NO2, OCH3, cyclohexyl either in ortho-, para- or meta-. position.

According to another embodiment of the present invention said coumarin fluorescent probe is selected from the group above wherein $R^1$ is $N[(CH_2)nCH_3]_2$ with n=4 and $R^2$ is H, F, Cl, Br, NO2, OCH3, cyclohexyl either in ortho-, para- or meta-. position.

According to another embodiment of the present invention said coumarin fluorescent probe is selected from the group above wherein $R^1$ is $N[(CH_2)nCH_3]_2$ with n=5 and $R^2$ is H, F, Cl, Br, NO2, OCH3, cyclohexyl either in ortho-, para- or meta-. position.

According to another embodiment of the present invention said coumarin fluorescent probe is 7-(Diethylamino)-2-oxo-N-((pyridin-2-yl)methyl)-2H-chromene-3-carboxamide having the following structural formula:

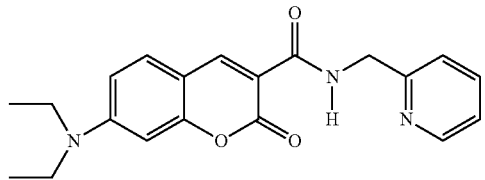 [SMILES: CCN(CC)c1ccc2cc(C(=O)NCc3ccccn3)c(=O)oc2c1]

The coumarin fluorescent probe may be used for example in organic solvents as EtOH, MeOH, DMSO mixed to buffer solutions as PBS or Hepes. In one embodiment the coumarin fluorescent probe is used in a solution of HEPES:DMSO.

The coumarin fluorescent probes will be used preferably in a concentration range between 0.1 and 10 μM, for example 1, 2.5, 5.0, 9 μM. The inventors found that in this range there is a direct correlation between the concentration of free copper in the sample and the fluorescence emission, the excitation wavelength ($\lambda_{ex}$) is for example 430 nm and the emission wavelength ($\lambda_{em}$) 490 nm.

Figure 1:
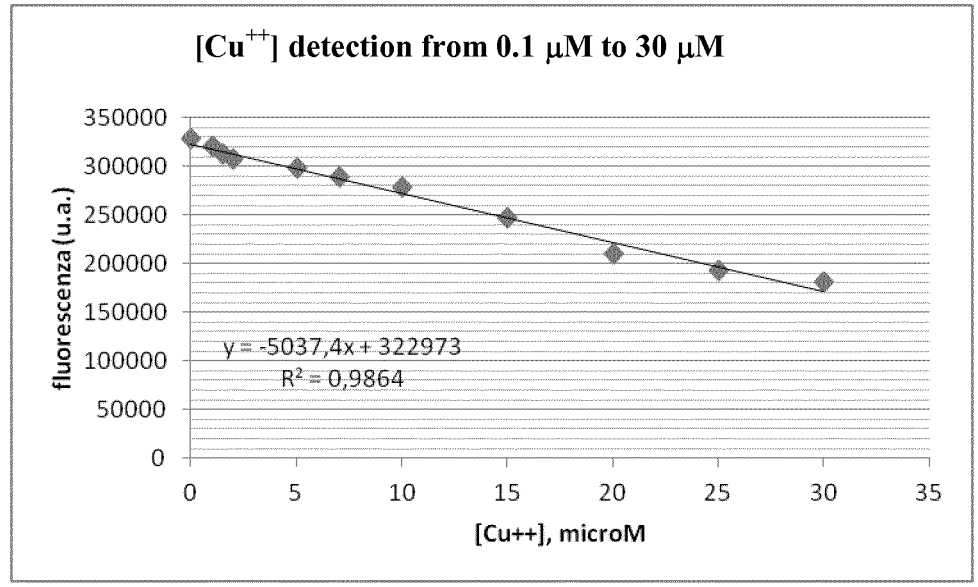
FIG. 1. Calibration curve of the coumarin fluorescent probe 7-(Diethylamino)-2-oxo-N-((pyridin-2-yl)methyl)-2H-chromene-3-carboxamide in presence of $Cu^{++}$ ($10^{-4}$ M) in HEPES:DMSO 9:1 ($\lambda_{ex}$=430 nm, $\lambda_{em}$ 490 nm).

In order to determine the concentration of the free copper in the serum the step b) may comprise a further step of preparing a calibration curve binding the decrease of fluorescence to the concentration of free copper. To prepare the curve one or more aliquots with a known concentration of free copper may be used. Preferably this curve will be in the range between 0.1 and 10 μM (see FIG. 1).

As previously reported in patients affected by Alzheimer's Disease, serum copper not bound to ceruloplasmin ('free' copper) appears elevated and the increase, although slight but normally sufficient to distinguish Alzheimer's Disease patients from healthy elderly subjects (also in the early stages of the disease).

Hence it is an object of the present invention an in vitro method for the confirmation of a clinical diagnosis of Alzheimer's Disease in a patient suspected of having Alzheimer's Disease comprising the same steps a) and b) and a further step c) of comparing the value determined in step b) with a threshold value (cut-off), wherein a higher concentration of free copper confirms the clinical diagnosis of Alzheimer's Disease.

The threshold value (cut-off) of free copper may be determined for example by means of ROC curves (Receiver Operating Characteristic) obtained by processing the concentrations of a set of samples (statistically significant) of healthy individuals and individuals with Alzheimer's Disease. Through such processing were obtained for example certain threshold values between 0.5 and 50 μM, for example 1, 5, 8, 10, 15, 20, 30, 35, 40, 45.

Preferably said diagnosis method will be used as a confirming test for a clinical diagnosis of Alzheimer's Disease in a patient suspected of having Alzheimer's Disease with a 'copper phenotype dysfunction', which is exhibited approximately by 60% of Alzheimer's Disease patients with the sporadic form of the disease.

Figure 5:
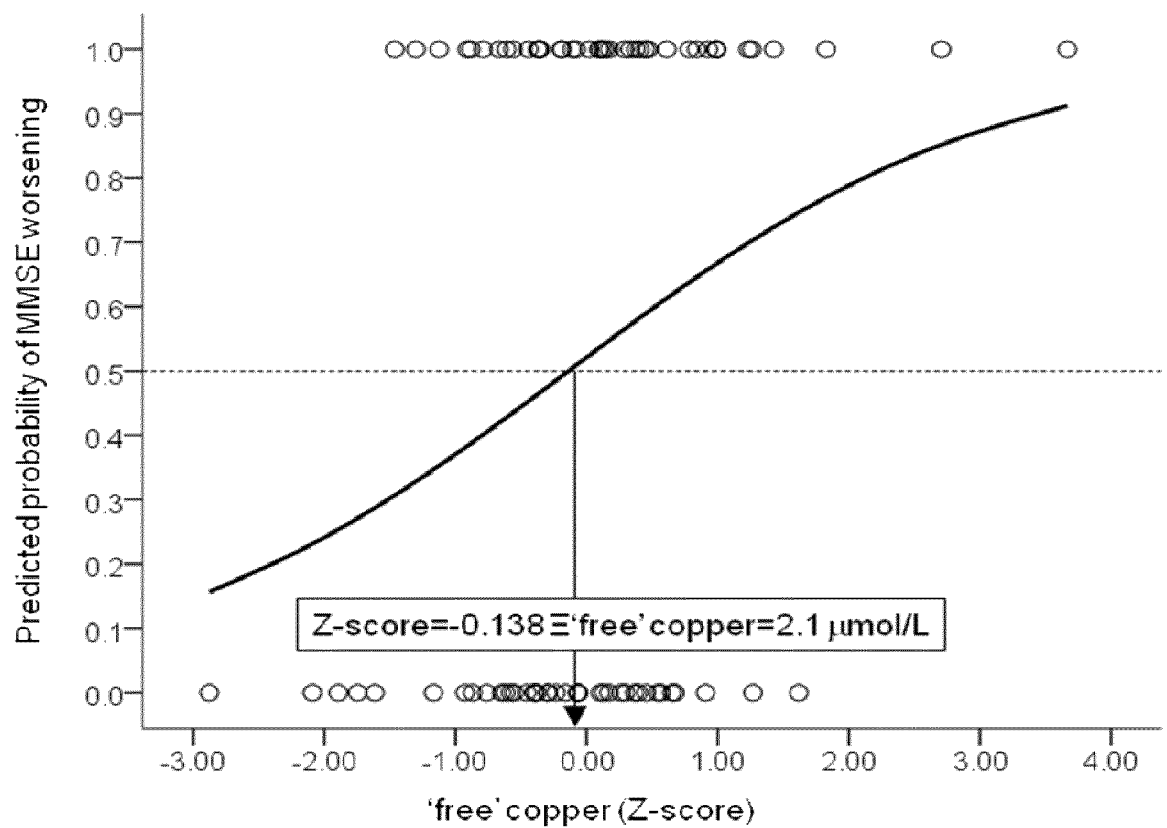
FIG. 5. Model to predict the probability of Mini-mental State Examination worsening in patients affected by Alzheimer's Disease according to free serum copper levels. Circle represent the value of free serum copper of the patients. The line represents the model of the predicted probability of Mini-mental State Examination E worsening. Free copper levels in individual Alzheimer's Disease patients are expressed in z-score, i.e. in terms of standard deviations from their mean value. Those patients from the current study panel who had a z-score higher than −0.138, corresponding to a free copper value of 2.1 µmol/L, had an increased probability to worsen than those patients who had their 'free' copper values below such levels.

As showed by Squitti et al., *Neurology* (2009) to monitor the prognosis of Alzheimer's Disease in a patient as well as to predict the conversion form Mild Cognitive Impairment (Mild cognitive impairment) to Alzheimer's disease it is important to determine the concentration of free copper in the serum of said patient. Specifically, free copper predicts the annual change in Mini Mental State Examination (MMSE), adjusted for the baseline Mini Mental State Examination by means of a linear regression model: it raised the 2.4% of predicted probability of Mini Mental State Examination worsening by only sex, age and education, to a predicted probability of Mini Mental State Examination worsening of 23%: (OR=1.23; 95% CI=1.03-1.47; p=0.022), when the annual change in Mini Mental State Examination was divided into <3 or >=3 points; it this case free copper was the only predictor of a more severe decline (FIG. 5).

The clinical condition of Mild cognitive impairment is characterized by memory impairments, verifiable via objective measures, not yet granting the definition of dementia. The importance of an accurate diagnosis lies in the fact that, despite the mildness of the condition, Mild cognitive impairment is normally considered as a precursor of Alzheimer's disease. This is due by the high statistical rate of progression from Mild cognitive impairment to Alzheimer's Disease.

Figure 6:
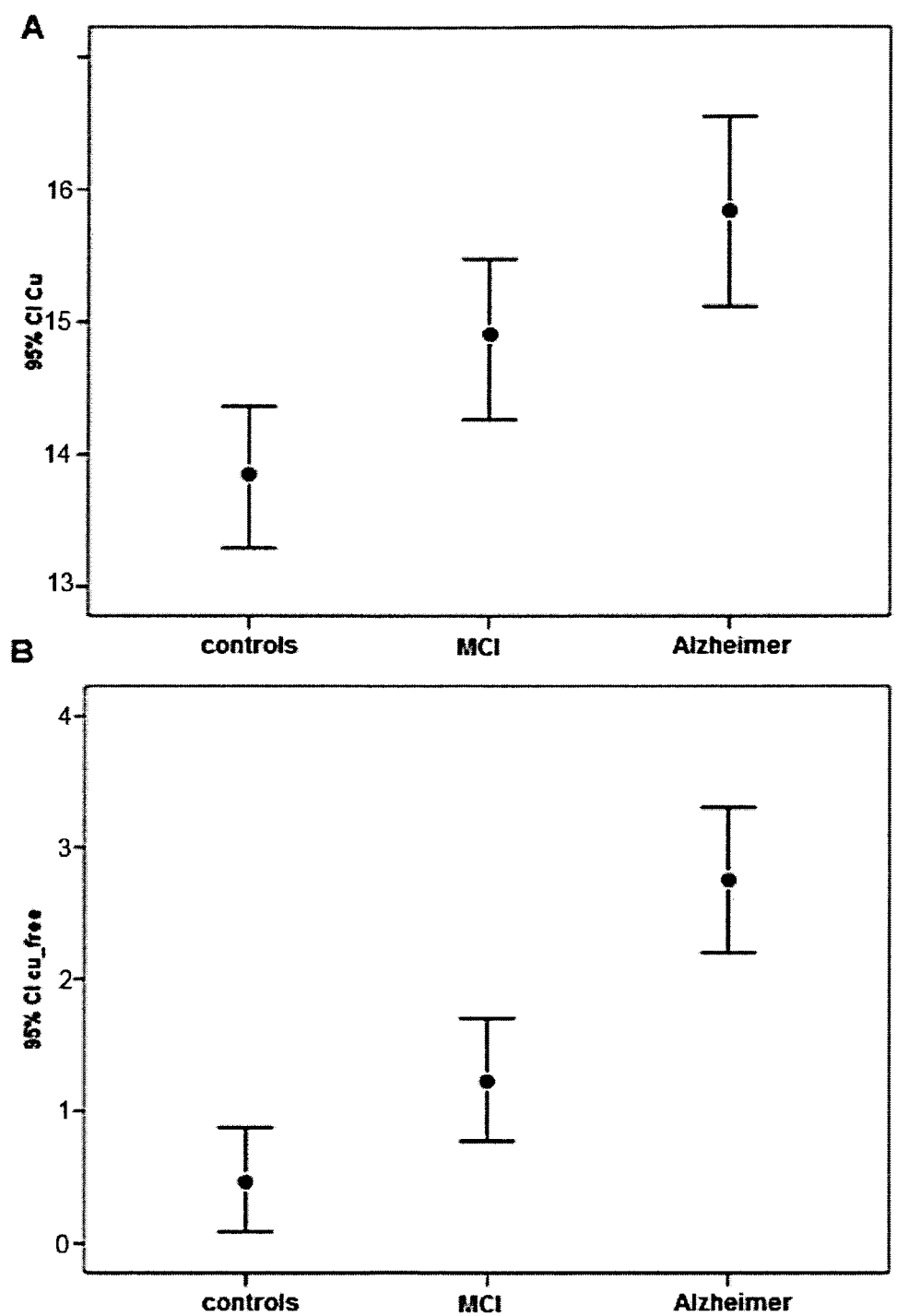
FIGS. 6A and 6B. Free copper distinguishes Mild cognitive impairment subjects from Healthy controls and Patients with Alzheimer. When the Alzheimer's Disease group was also considered, copper (FIG. 6A) and free copper (FIG. 6B) showed a clear gradient from healthy to Alzheimer's Disease patients passing through Mild cognitive impairment subjects. This gradient was more evident for free copper (eta-squared=14.5%) than for total copper (eta-squared=4.9%), due to the steep increase of free copper in the Alzheimer's Disease group (Squitti et al Journal Alz. Disease 2011).
Figure 7:
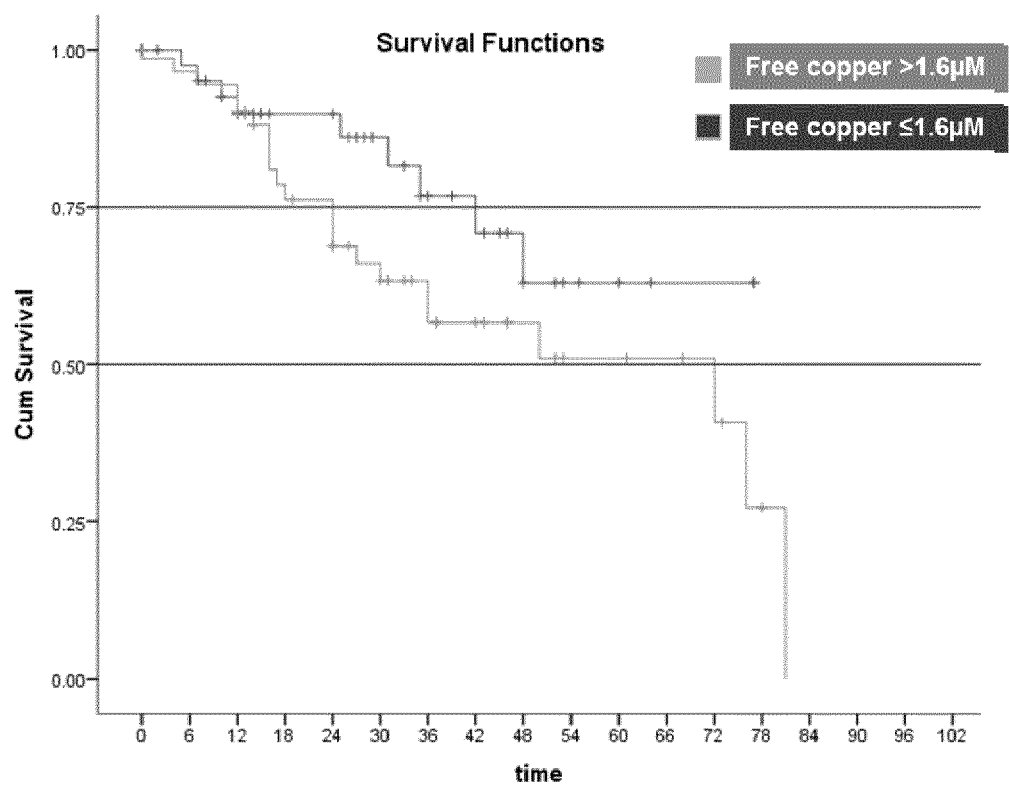
FIG. 7. Free copper can also predict the percentage of subjects complain Mild cognitive impairment who will develop full diagnosis of Alzheimer's Disease dementia. Mild cognitive impairment subjects with free copper >1.6 µM have a higher percentage of conversion to Alzheimer's Disease, that is 17% for year, with respect to those Mild cognitive impairment subjects with a free copper ≤1.6 µM, that is 10% per year. Kaplan-Meier statistical analysis confirms that Mild cognitive impairment subjects with free copper >1.6 µM have an higher rate of conversion to Alzheimer's Disease than those with free copper ≤1.6 µM, being their percentage of conversion in Alzheimer's Disease between 24-35% within the first two years, compared to 25-30% of those Mild cognitive impairment subjects with a free copper ≤1.6 µM convert within 3 years and an half. Noteworthy, limiting the analysis to the five year of follow-up, the percentage of conversion to Alzheimer's Disease in the Mild cognitive impairment subjects with a free copper ≤1.6 µM is less than 50%, while in the Mild cognitive impairment cohort with free copper >1.6 µM half of the patients convert within 4-6 years.

Normally, the annual conversion rate from a healthy condition to Alzheimer's Disease ranges from 0.17% to 3.86%. The conversion rate from Mild cognitive impairment to Alzheimer's Disease is remarkably higher, ranging from 6% to 40% depending on the clinical series. In some cases, Mild cognitive impairment can be a benign condition, with no progression into dementia. Free copper discriminates Mild cognitive impairment subjects from healthy control individuals, as revealed by comparing the means of the two groups (FIG. 6). Free copper can also predict the percentage of subjects complain Mild cognitive impairment who will develop full diagnosis of Alzheimer's Disease dementia. Mild cognitive impairment subjects with free copper >1.6 μM have a higher percentage of conversion to Alzheimer's disease, that is 17% for year, with respect to those Mild cognitive impairment subjects with a free copper ≤1.6 μM, that is 10% per year. Kaplan-Meier statistical analysis confirms that Mild cognitive impairment subjects with free copper >1.6 μM have an higher rate of conversion to Alzheimer's Disease than those with free copper ≤1.6 μM, being their percentage of conversion in Alzheimer's disease between 24-35% within the first two years, compared to 25-30% of those Mild cognitive impairment subjects with a free copper ≤1.6 μM convert within 3 years and an half. Noteworthy, limiting the analysis to the five year of follow-up, the percentage of conversion to Alzheimer's Disease in the Mild cognitive impairment subjects with a free copper ≤1.6 μM is less than 50%, while in the Mild cognitive impairment cohort with free copper >1.6 μM 50% of the patients convert within 4-6 years (FIG. 7).

Hence it is a further object of the present invention an in vitro method for determining the concentration of free copper for the prediction of the conversion form Mild Cognitive Impairment (MCI) to Alzheimer's disease in a patient suffering of Mild Cognitive Impairment comprising the steps a) and b) described above and a further step c) of comparing the value determined in step b) with a threshold value (cut-off), wherein a higher concentration of free copper indicates the conversion from Mild Cognitive Impairment to Alzheimer's disease. This threshold value is for example between 0.5 and 3 μM, preferably 1.6 μM.

Steps a) and b) of said prediction method may be performed according to any embodiments of steps a) and b) as disclosed above.

A further object of the present invention is an in vitro method for the prognosis of Alzheimer's Disease in a patient wherein the steps a) and b) of the method according to any embodiments of steps a) and b) as disclosed above are carried on more samples of said patient collected in different moments and the quantification of data obtained from each sample are compared one to the other thus constructing a progression in time of the concentration of free copper in the serum samples of said patient.

A further object of the invention is a kit for the detection of free copper in serum comprising one or more filter devices with a membrane filter having a pore size between 0.1-0.5 μm, preferably between 0.1-0.2 μm, more preferably between 0.1-0.15 μm and one or more coumarin fluorescent probes.

The filter device of the kit may be any filter devices disclosed in the present description as for example a filter device with a bottom 2 including one or more microchannels, a lid 3, wherein the membrane filter 4 is incorporated into said lid and over said microchannels. In the kit may be used any membrane filters in combination with any coumarin fluorescent probes disclosed in the present description.

In one embodiment the kit further comprising one or more aliquot of controls having a known title of free copper, these controls may be used to prepare a calibration curve.

EXAMPLES

1. Synthesis of Coumarin Fluorescent Probe

Synthesis of the coumarin fluorescent probe was carried out as reported in Hyo Sung Jung et al. (J. Am. Chem. Soc. 2009), herein incorporated by reference, using the following scheme:

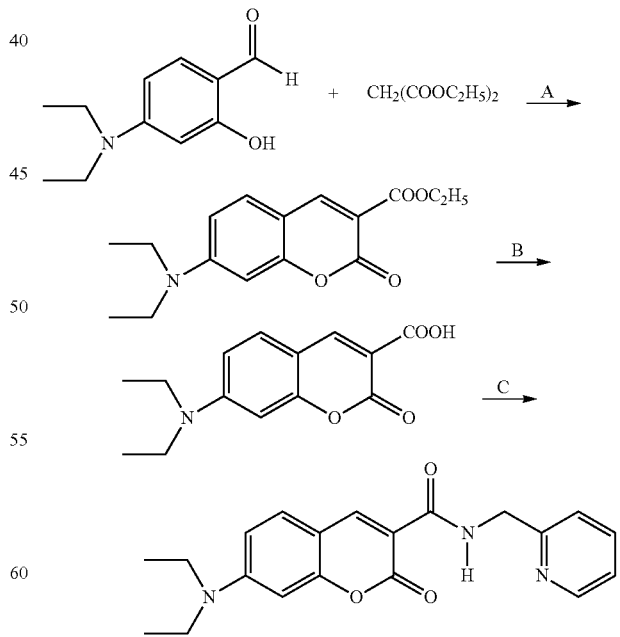

Reagents:
A: piperidine, Acectic acid;
B: NaOH/H2O; EtOH, HCl;
C: 2-(aminomethyl)-pyridine, DCC/DMAP.

2. Evaluation of Spectroscopic Properties of Coumarin Fluorescent Probe

Probe absorption and emission spectra were recorded with LS55 PerkinElmer spectrofluorimeter using several solvents. Organic solvents evaluated are EtOH, MeOH, DMSO in PBS, $H_2O$ or Hepes buffers at pH 7.2. Considering both the behaviour of the probe in an aqueous environment and the evaluation of the data of the spectra, best results were obtained with a mixture of Hepes:DMSO (95:5). Starting from these data, several assays were carried out to establish the appropriate concentration of the probe that could be useful for the binding of [Cu++] in the biological sample. Calibration curve of the fluorescent probe in presence of Cu++($10^{-4}$ M) in HEPES:DMSO 9:1 ($\lambda$ex=430 nm, $\lambda$em 490 nm) is showed in FIG. 1. It has been demonstrated the useful concentration for the probe in tested solution.

3. Optimization of Spectroscopic and Biological Properties

Figure 2:
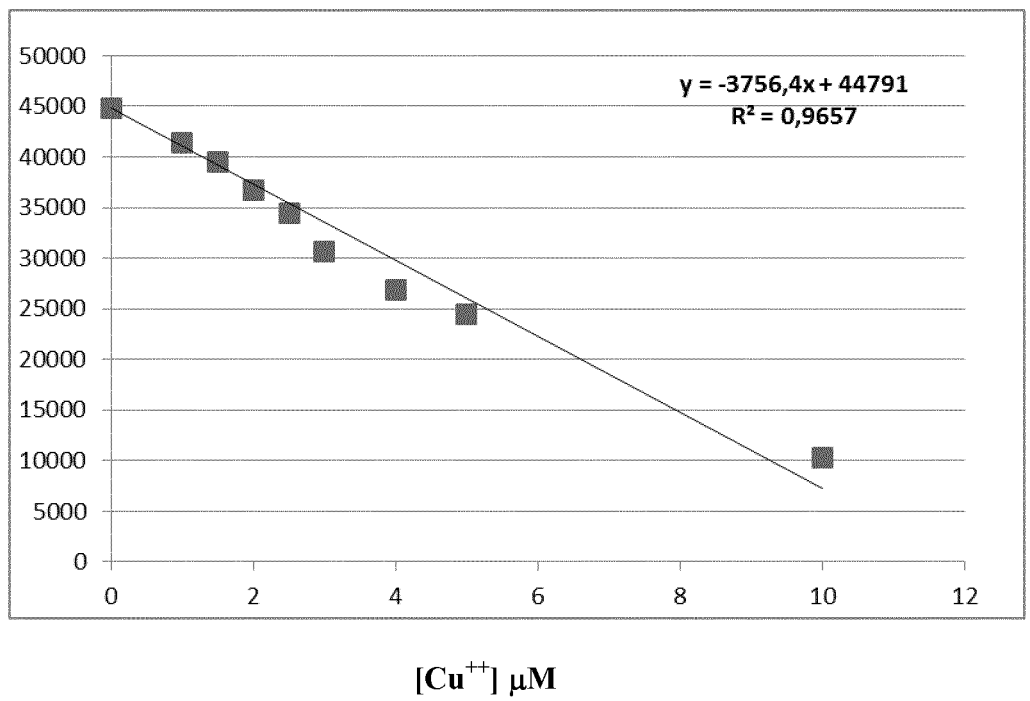
FIG. 2. Calibration curve of the coumarinic fluorescent probe 7-(Diethylamino)-2-oxo-N-((pyridin-2-yl)methyl)-2H-chromene-3-carboxamide in presence of $Cu^{++}$ ($10^{-5}$ M) with HEPES:DMSO 95:5 ($\lambda_{ex}$=430 nm, $\lambda_{em}$ 495 nm).

It was thought to improve the method using a 96-well plate. This allows short working times and a most practical method for the different operations. For this purpose we used a PerkinElmer Victor III plate reader to check the experimental conditions of the probe. The excitation and the emission wavelengths are obviously similar to those that we have previously determined with the fluorimeter ($\lambda_{ex}$=380 nm, $\lambda_{em}$=495 nm). The optimal dose is $10^{-5}$ M. Indeed the calibration curve with the probe at the concentration of $10^{-4}$ M, using the VICTOR III plate reader, gave a good correlation but a too high fluorescence signal and the differences were not appreciable, especially at lower doses. Therefore, probe calibration curves were built with increasing doses of $CuCl_2$ to evaluate the switch-off of the probe and to find an equation useful to determinate the concentration of copper ion. These doses of $CuCl_2$ were used: 0, 0.5, 1, 1.5, 2, 2.5, 3, 4, 5, 7, 10, 15, 20 µM. Calibration curve for the fluorescent probe in presence of $Cu^{++}$ ($10^{-5}$ M) with HEPES:DMSO 95:5 ($\lambda_{ex}$=430 nm, $\lambda_{em}$495 nm) is shown in FIG. 2. A very good correlation was found within 0.1 µM-10 µM.

4. Comparative Examples Showing Several Methods to Purify Free Copper in Serum Sample Blood samples with known concentrations of free copper were treated using the following steps:
A. Ultracentrifuge, 1 h, 40000 rpm
B. Treatment with acetonitrile and ultracentrifuge
C. Step 1: treatment of the sample with acetonitrile (10%); step 2: centrifuge, 30 min, 14,000 rpm; step 3: different types of filtering devices:
  VIVASPIN 500 centrifugal concentrator with a 5000 Dalton cutoff, PEC (polyethersulfone) membrane.
  VIVASPIN 2 centrifugal concentrator with a 10,000 Dalton cutoff, PES (polyethersulfone) membrane.
  VIVASPIN e centrifugal concentrator with a 10,000 Dalton cutoff, HYDROSART RC (regenerated cellulose) membrane.
We have obtained these results with these filters:
  Sample number 1874=0.904 µM
  Sample number 1876=6.55 µM
  Sample number 2045=4.97 µM
Several aspects have been evidenced using these filters:
1. adhesion of the filter used (copper loss estimated between 10% and 20%, also for the samples for which the dosage has been done);
2. nonspecific interaction between probe and serum.
These problems have been overcome using for example the microfluidic device at disclosed in Thorslund S. et al, *Biomed Microdevices* (2006) 8: 73-79 herein incorporated by reference wherein a policarbonate membrane is used.

Figure 3:
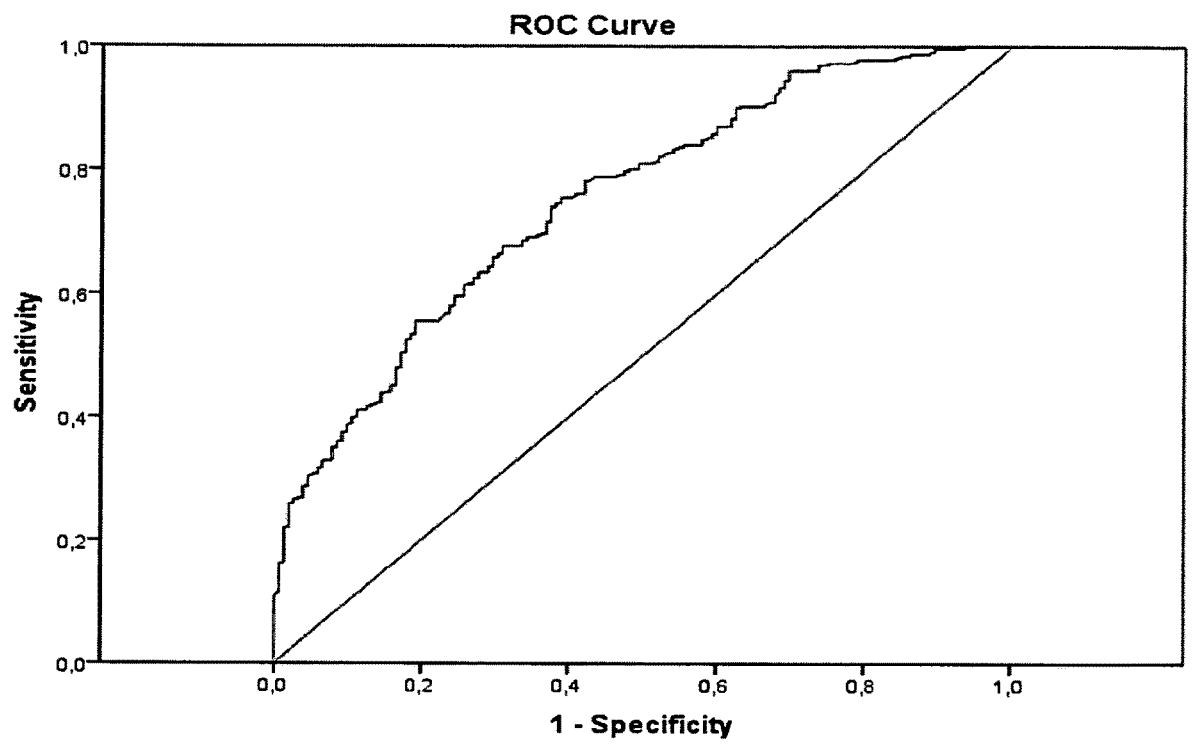
FIG. 3. Receiver operating characteristic (ROC) curve. 702 samples have been analysed according to one embodiment of the present invention. The curve shows that using the present invention a diagnosis of Alzheimer's disease can be obtained with high specificity (80%) and discrete sensitivity (60%).

5. Evaluate the Sensitivity and the Specificity of the Method by Using ROC Curve The study was approved by the IRB and all participants or legal guardians signed an informed consent. Table 1 reported the demographic, clinical and molecular characteristics of the study population used to set up the Receiver operating characteristic (ROC) curve. 702 samples have been analyzed according to one embodiment of the present invention. The ROC curve shows that using the present invention a diagnosis of Alzheimer's Disease can be obtained with high specificity (80%) and discrete sensitivity (60%). The Alzheimer's Disease patient sample consisted of individuals with a diagnosis of probable Alzheimer's Disease, (NINCDS-Alzheimer's DiseaseRDA criteria), who had a Mini-Mental State Examination score of 25 or less, who were admitted to the Department of Neuroscience, Fatebenefratelli Hospital, Isola Tiberina, in Rome, centre between Jan. 2002 and Jun. 2011. Approximately, 85% of Alzheimer's Disease patients included in this investigation had been involved in a previous studies. The two groups were matched for sex, but slightly differed for age, patients being on average. Alzheimer's disease patients underwent neurologic, neuroimaging (Magnetic Resonance Imaging or computerized axial tomography) and extensive neuropsychological evaluation as well as routine laboratory tests. The control sample consisted of elderly volunteers with no clinical evidence of neurological and psychiatric disease. Both patients and controls were evaluated for presence of conditions known to affect copper metabolism and biological variables of oxidative stress (e.g. diabetes mellitus, inflammatory diseases, recent history of heart or respiratory failure, chronic liver or renal failure, malignant tumors and a recent history of alcohol abuse) were excluded. All participants underwent assays of trace metals, biological variables of oxidative stress and APOE genotyping. The ROC curve (FIG. 3) revealed that free copper has a good reliability as a supporting test for the diagnosis of Alzheimer's Disease. This concept is reinforced when free copper sensitivity and specificity is compared with those of the most two supporting test used in clinical routine to pose the diagnosis of Alzheimer's Disease, i.e. Medial temporal lobe atrophy (MTA) and APOE (Table 2).

The separation of serum from the whole blood of said samples was carried out using the microfluidic device disclosed in Thorslund S. et al, Biomed Microdevices (2006).
These data suggest that:
  this method is useful for a supporting test for Alzheimer's Disease diagnosis, accordingly to the NINCDS-Alzheimer's Disease RDA criteria recently revised Dubois et al Lancet Neurology (2007).
  This method is better than other methods such as APOE and MTA to define Alzheimer's Disease diagnosis starting from early stage of both neurodegenerative pathologies as reported in Table 2.

TABLE 1

Demographic, clinical and molecular characteristics of the study population.

|  | Alzheimer's Disease patients (n = 399) | Controls (n = 303) | Significance |
| --- | --- | --- | --- |
| Age, years | 74.9 ± 8.1 | 66.5 ± 10.5 | p < 0.001 |
| Sex (female), % | 67.7 | 68.3 | p = 0.889 |
| MMSE score | 19.5 ± 4.5 | 28.6 ± 1.3 | p < 0.001 |
| APOE e4 carriers, % | 36.7 | 11.6 | p < 0.001 |
| Education, years | 8.9 ± 5.0 | 9.5 ± 4.5 | p = 0.634 |
| Copper, μmol/L | 14.98 ± 3.14 | 13.05 ± 2.98 | p < 0.001 |
| Ceruloplasmin, mg/dL | 26.88 ± 5.09 | 26.90 ± 5.20 | p = 0.959 |
| Free_copper, μmol/L | 2.24 ± 2.25 | 0.28 ± 2.32 | p < 0.001 |

TABLE 2

Sensitivity and specificity of medial temporal atrophy (MTA) APOE, Free copper.

|  | Sensitivity - Alzheimer's Disease vs. controls (95% CI) | Specificity - Alzheimer's Disease vs. controls (95% CI) |
| --- | --- | --- |
| MTA | 37% (27-47) | 92% (86-98) |
| APOE | 37% (27-47) | 91% (85-97) |
| Free copper | 51% (41-61) | 88% (81-95) |

Free copper has a higher reliability than MTA and APOE to discriminate Alzheimer's Disease patients from controls, which are the most used Neuroimaging (MTA) and genetic test (APOE) supporting and non-invasive markers used to pose the diagnosis of Alzheimer's Disease.

The invention claimed is:

1. An in vitro method for determining the concentration of free copper in a blood sample comprising the following steps:
   a) separating serum from whole blood of said sample with a filter device comprising a membrane filter having a pore size between 0.1-0.5 μm using a filtering speed between 200 and 500 microliters per minute to provide a serum sample, wherein said filter device is a poly (dimethylsiloxane) (PDMS) casted device and said membrane filter is a polycarbonate membrane filter, and
   b) determining the concentration of free copper in the serum sample obtained in step a) using a coumarin fluorescent probe.

2. The method according to claim 1, wherein said membrane filter has a pore size between 0.1-0.2 μm.

3. The method according to claim 1, wherein said coumarin fluorescent probe is used in a concentration range between 0.1 and 10 μM.

4. The method according to claim 1, wherein said coumarin fluorescent probe is used in a solution of HEPES: DMSO.

5. The method according to claim 1, wherein said step b) further comprises preparing a calibration curve.

6. The method according to claim 1, wherein an excitation wavelength ($\lambda_{ex}$) of 430 nm and an emission wavelength ($\lambda_{em}$) of 490 nm is used in said step b).

7. The method according to claim 1, wherein said filter device further comprises:
   a bottom including one or more microchannels; and
   a lid, wherein said membrane filter is incorporated into said lid and over said one or more microchannels.

8. The method according to claim 1, wherein said coumarin fluorescent probe is selected from the group consisting of compounds having the following general structural formula:

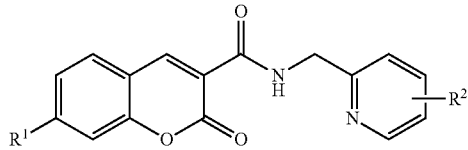

wherein $R^1$ is $N[(CH_2)_nCH_3]_2$ and n is from 0 to 5; and $R^2$ is H, F, Cl, Br, $NO_2$, $OCH3$, or cyclohexyl.

9. The method according to claim 8, wherein said coumarin fluorescent probe has the following structural formula:

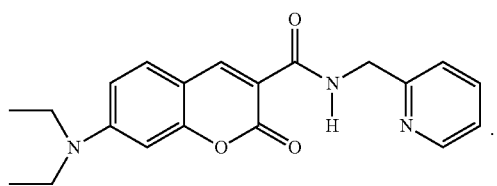 [SMILES: CCN(CC)c1ccc2cc(C(=O)NCc3ccccn3)c(=O)oc2c1]

10. The method according to claim 1, wherein said blood sample is obtained from a patient suffering from Mild Cognitive Impairment (MCI).

11. The method according to claim 1, wherein said blood sample has >1.6 μM free copper.

12. An in vitro method for determining progression over time of free copper concentration in a blood sample from a patient suffering from mild cognitive impairment, comprising the following steps:
   a) separating serum from whole blood of said sample with a filter device comprising a membrane filter having a pore size between 0.1-0.5 μm using a filtering speed between 200 and 500 microliters per minute to provide a serum sample, wherein said filter device is a poly (dimethylsiloxane) (PDMS) casted device and said membrane filter is a polycarbonate membrane filter;
   b) determining the concentration of free copper in the serum sample obtained in step a) using a coumarin fluorescent probe; and
   c) subsequently repeating steps a) and b) at a different time.

13. The method according to claim 12, wherein said patient's blood has greater than 1.6 μM free copper.

14. An in vitro method for determining progression over time of free copper concentration in a blood sample from a patient with a copper phenotype dysfunction, comprising the following steps:
   a) separating serum from whole blood of said sample with a filter device comprising a membrane filter having a pore size between 0.1-0.5 μm using a filtering speed between 200 and 500 microliters per minute to provide a serum sample, wherein said filter device is a poly (dimethylsiloxane) (PDMS) casted device and said membrane filter is a polycarbonate membrane filter;

b) determining the concentration of free copper in the serum sample obtained in step a) using a coumarin fluorescent probe; and
c) subsequently repeating steps a) and b) at a different time.

15. The method according to claim 14, wherein said patient's blood has greater than 1.6 µM free copper.

* * * * *